(12) United States Patent
Wood, Jr.

(10) Patent No.: US 8,361,056 B2
(45) Date of Patent: Jan. 29, 2013

(54) SYSTEM WITH A RESERVOIR FOR PERFUSION MANAGEMENT

(75) Inventor: Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

(21) Appl. No.: 12/930,916

(22) Filed: Jan. 18, 2011

(65) Prior Publication Data

US 2011/0208120 A1  Aug. 25, 2011

Related U.S. Application Data (63) Continuation of application No. 10/827,576, filed on Apr. 19, 2004, and a continuation of application No. 10/827,578, filed on Apr. 19, 2004, and a continuation of application No. 10/827,390, filed on Apr. 19, 2004, and a continuation of application No.

(Continued)

(51) Int. Cl.
*A61M 25/00* (2006.01)
*A61M 37/00* (2006.01)
(52) U.S. Cl. .......... 604/528; 604/288.04; 604/523; 604/264; 604/93.01
(58) Field of Classification Search ........... 604/93.01, 604/164.01, 187, 194–196, 239, 264, 272
See application file for complete search history.

(56) References Cited

U.S. PATENT DOCUMENTS

| | | |
|---|---|---|
| 3,391,697 A | 7/1968 | Greatbatch |
| 3,837,339 A | 9/1974 | Aisenberg et al. |
| 4,267,831 A | 5/1981 | Aguilar |
| 4,583,190 A | 4/1986 | Salb |
| 4,585,652 A | 4/1986 | Miller et al. |
| 4,628,928 A | 12/1986 | Lowell |
| 4,714,460 A | 12/1987 | Calderon |
| 4,717,381 A | 1/1988 | Papantonakos |
| 4,750,488 A | 6/1988 | Wuchinich et al. |
| 4,763,667 A | 8/1988 | Manzo |
| 4,769,006 A | 9/1988 | Papantonakos |
| 4,771,772 A | 9/1988 | DeWitt |
| 4,795,434 A | 1/1989 | Kujawski |
| 4,800,898 A | 1/1989 | Hess et al. |
| 4,817,601 A | 4/1989 | Roth et al. |
| 4,871,351 A | 10/1989 | Feingold |
| 4,905,689 A | 3/1990 | Stack et al. |
| 4,944,659 A | 7/1990 | Labbe et al. |
| 4,994,071 A | 2/1991 | MacGregor |
| 5,019,372 A | 5/1991 | Folkman et al. |
| 5,153,827 A | 10/1992 | Coutre et al. |
| 5,176,638 A | 1/1993 | Don Michael |
| 5,188,111 A | 2/1993 | Yates et al. |
| 5,234,457 A | 8/1993 | Andersen |
| 5,269,303 A | 12/1993 | Wernicke et al. |
| 5,279,607 A | 1/1994 | Schentag et al. |
| 5,310,404 A | 5/1994 | Gyory et al. |
| 5,314,451 A | 5/1994 | Mulier |
| 5,335,657 A | 8/1994 | Terry, Jr. et al. |
| 5,337,732 A | 8/1994 | Grundfest et al. |
| 5,338,625 A | 8/1994 | Bates et al. |

(Continued)

OTHER PUBLICATIONS

Mosby's Dictionary of Medicine, Nursing & Health Professions; "endoscopy"; 2009; Credo Reference. Web. Jun. 29, 2011; 1 page; Elsevier Health Sciences.

(Continued)

*Primary Examiner* — Victoria P Shumate (57) ABSTRACT

A system for perfusion management that monitors, maintains, diagnoses, or treats perfusion deficiencies.

21 Claims, 5 Drawing Sheets

Related U.S. Application Data

10/827,572, filed on Apr. 19, 2004, now Pat. No. 7,850,676, and a continuation of application No. 11/891,371, filed on Aug. 9, 2007, and a continuation of application No. 11/891,573, filed on Aug. 9, 2007, and a continuation of application No. 11/891,355, filed on Aug. 9, 2007, now Pat. No. 7,871,402, and a continuation of application No. 11/891,333, filed on Aug. 9, 2007, now Pat. No. 7,867,217, and a continuation of application No. 11/891,334, filed on Aug. 9, 2007, now Pat. No. 7,879,023, and a continuation of application No. 11/891,356, filed on Aug. 9, 2007.

U.S. PATENT DOCUMENTS

| Patent Number | | Date | Inventor(s) |
|---|---|---|---|
| 5,339,051 | A | 8/1994 | Koehler et al. |
| 5,353,807 | A | 10/1994 | DeMarco |
| 5,374,285 | A | 12/1994 | Vaiani et al. |
| 5,386,741 | A | 2/1995 | Rennex |
| 5,395,390 | A | 3/1995 | Simon et al. |
| 5,398,670 | A | 3/1995 | Ortiz et al. |
| 5,403,311 | A | 4/1995 | Abele et al. |
| 5,411,551 | A | 5/1995 | Winston et al. |
| 5,437,660 | A | 8/1995 | Johnson et al. |
| 5,476,450 | A | 12/1995 | Ruggio |
| 5,497,147 | A | 3/1996 | Arms et al. |
| 5,522,394 | A | 6/1996 | Zurbrugg |
| 5,551,953 | A | 9/1996 | Lattin et al. |
| 5,554,914 | A | 9/1996 | Miyazawa |
| 5,569,968 | A | 10/1996 | Lal et al. |
| 5,574,347 | A | 11/1996 | Neubauer |
| 5,593,434 | A | 1/1997 | Williams |
| 5,599,324 | A | 2/1997 | McAlister et al. |
| 5,610,488 | A | 3/1997 | Miyazawa |
| 5,624,398 | A | 4/1997 | Smith et al. |
| 5,632,754 | A | 5/1997 | Farley et al. |
| 5,643,296 | A | 7/1997 | Hundertmark et al. |
| 5,662,587 | A | 9/1997 | Grundfest et al. |
| 5,669,874 | A | 9/1997 | Feiring |
| 5,670,329 | A | 9/1997 | Oberhardt |
| 5,674,276 | A | 10/1997 | Andersen et al. |
| 5,688,269 | A | 11/1997 | Newton et al. |
| 5,695,457 | A | 12/1997 | St. Goar et al. |
| 5,697,967 | A | 12/1997 | Dinh et al. |
| 5,702,432 | A | 12/1997 | Chen et al. |
| 5,705,293 | A | 1/1998 | Hobson |
| 5,728,089 | A | 3/1998 | Lal et al. |
| 5,737,279 | A | 4/1998 | Carter |
| 5,782,798 | A | 7/1998 | Rise |
| 5,804,563 | A | 9/1998 | Still et al. |
| 5,807,395 | A | 9/1998 | Mulier et al. |
| 5,819,736 | A | 10/1998 | Avny et al. |
| 5,830,179 | A | 11/1998 | Mikus et al. |
| 5,830,207 | A | 11/1998 | Leeb et al. |
| 5,831,012 | A | 11/1998 | Nilsson et al. |
| 5,843,139 | A | 12/1998 | Goedeke et al. |
| 5,855,801 | A | 1/1999 | Lin et al. |
| 5,873,835 | A | 2/1999 | Hastings et al. |
| 5,908,027 | A | 6/1999 | Butterfield et al. |
| 5,921,982 | A | 7/1999 | Lesh et al. |
| 5,947,119 | A | 9/1999 | Reznick |
| 5,951,600 | A | 9/1999 | Lemelson |
| 5,954,675 | A | 9/1999 | Dellagatta |
| 5,964,773 | A | 10/1999 | Greenstein |
| 6,004,269 | A | 12/1999 | Crowley et al. |
| 6,016,449 | A | 1/2000 | Fischell et al. |
| 6,019,729 | A | 2/2000 | Itoigawa et al. |
| 6,022,316 | A | 2/2000 | Eppstein et al. |
| 6,053,873 | A | 4/2000 | Govari et al. |
| 6,086,528 | A | 7/2000 | Adair |
| 6,102,845 | A | 8/2000 | Woodard et al. |
| 6,111,520 | A | 8/2000 | Allen et al. |
| 6,128,538 | A | 10/2000 | Fischell et al. |
| 6,134,474 | A | 10/2000 | Fischell et al. |
| 6,149,603 | A | 11/2000 | Parker |
| 6,159,230 | A | 12/2000 | Samuels |
| 6,164,284 | A | 12/2000 | Schulman et al. |
| 6,170,488 | B1 | 1/2001 | Spillman, Jr. et al. |
| 6,179,789 | B1 | 1/2001 | Tu et al. |
| 6,185,452 | B1 | 2/2001 | Schulman et al. |
| 6,186,986 | B1 | 2/2001 | Berg et al. |
| 6,187,599 | B1 | 2/2001 | Asher et al. |
| 6,197,013 | B1 | 3/2001 | Reed et al. |
| 6,219,577 | B1 | 4/2001 | Brown, III et al. |
| 6,221,099 | B1 | 4/2001 | Andersen et al. |
| 6,240,312 | B1 | 5/2001 | Alfano et al. |
| 6,248,345 | B1 | 6/2001 | Goldenheim et al. |
| 6,249,076 | B1 | 6/2001 | Madden et al. |
| 6,255,361 | B1 | 7/2001 | Rajagopalan et al. |
| 6,278,379 | B1 | 8/2001 | Allen et al. |
| 6,295,990 | B1 | 10/2001 | Lewis et al. |
| 6,296,638 | B1 | 10/2001 | Davison et al. |
| 6,322,532 | B1 | 11/2001 | D'Sa et al. |
| 6,337,997 | B1 | 1/2002 | Rise |
| 6,372,248 | B1 | 4/2002 | Qin et al. |
| 6,383,162 | B1 | 5/2002 | Sugarbaker |
| 6,384,741 | B1 | 5/2002 | O'Leary, Sr. |
| 6,385,472 | B1 | 5/2002 | Hall et al. |
| 6,398,280 | B1 | 6/2002 | Parker et al. |
| 6,400,980 | B1 | 6/2002 | Lemelson |
| 6,402,678 | B1 | 6/2002 | Fischell et al. |
| 6,409,674 | B1 | 6/2002 | Brockway et al. |
| 6,431,171 | B1 | 8/2002 | Burton |
| 6,436,120 | B1 | 8/2002 | Meglin |
| 6,442,413 | B1 | 8/2002 | Silver |
| 6,450,937 | B1 | 9/2002 | Mercereau et al. |
| 6,453,199 | B1 | 9/2002 | Kobozev |
| 6,475,639 | B2 | 11/2002 | Shahinpoor et al. |
| 6,490,483 | B2 | 12/2002 | Willis |
| 6,497,714 | B1 | 12/2002 | Ishikawa et al. |
| 6,512,949 | B1 | 1/2003 | Combs et al. |
| 6,512,950 | B2 | 1/2003 | Li et al. |
| 6,514,237 | B1 | 2/2003 | Maseda |
| 6,530,950 | B1 | 3/2003 | Alvarado et al. |
| 6,547,825 | B1 | 4/2003 | Shimizu et al. |
| 6,548,982 | B1 | 4/2003 | Papanikolopoulos et al. |
| 6,554,798 | B1 | 4/2003 | Mann et al. |
| 6,575,969 | B1 | 6/2003 | Rittman, III et al. |
| 6,585,763 | B1 | 7/2003 | Keilman et al. |
| 6,591,137 | B1 | 7/2003 | Fischell et al. |
| 6,592,567 | B1 | 7/2003 | Levin et al. |
| 6,597,954 | B1 | 7/2003 | Pless et al. |
| 6,607,553 | B1 | 8/2003 | Healy et al. |
| 6,616,676 | B2 | 9/2003 | Bashiri et al. |
| 6,623,519 | B2 | 9/2003 | Edwin et al. |
| 6,632,216 | B2 | 10/2003 | Houzego et al. |
| 6,638,273 | B1 | 10/2003 | Farley et al. |
| 6,648,908 | B2 | 11/2003 | Dobak, III et al. |
| 6,666,860 | B1 | 12/2003 | Takahashi |
| 6,669,683 | B2 | 12/2003 | Santini, Jr. et al. |
| 6,673,042 | B1 | 1/2004 | Samson et al. |
| 6,673,363 | B2 | 1/2004 | Luo et al. |
| 6,679,893 | B1 | 1/2004 | Tran |
| 6,709,388 | B1 | 3/2004 | Mosse et al. |
| 6,711,423 | B2 | 3/2004 | Colvin, Jr. |
| 6,712,835 | B2 | 3/2004 | Mazzocchi et al. |
| 6,719,684 | B2 | 4/2004 | Kim et al. |
| 6,723,092 | B2 | 4/2004 | Brown et al. |
| 6,733,485 | B1 | 5/2004 | Whitehurst et al. |
| 6,735,474 | B1 | 5/2004 | Loeb et al. |
| 6,735,475 | B1 | 5/2004 | Whitehurst et al. |
| 6,743,211 | B1 | 6/2004 | Prausnitz et al. |
| 6,754,536 | B2 | 6/2004 | Swoyer et al. |
| 6,755,802 | B2 | 6/2004 | Bell |
| 6,755,803 | B1 | 6/2004 | Le et al. |
| 6,764,441 | B2 | 7/2004 | Chiel et al. |
| 6,773,429 | B2 | 8/2004 | Sheppard, Jr. et al. |
| 6,797,522 | B1 | 9/2004 | Still et al. |
| 6,802,811 | B1 | 10/2004 | Slepian |
| 6,824,508 | B2 | 11/2004 | Kim et al. |
| 6,824,510 | B2 | 11/2004 | Kim et al. |
| 6,824,561 | B2 | 11/2004 | Soykan et al. |
| 6,849,183 | B2 | 2/2005 | Gorsuch et al. |
| 6,855,115 | B2 | 2/2005 | Fonseca et al. |
| 6,860,867 | B2 | 3/2005 | Seward et al. |

| | | |
|---|---|---|
| 6,861,001 B2 | 3/2005 | Lee et al. |
| 6,875,209 B2 | 4/2005 | Zvuloni et al. |
| 6,882,881 B1 | 4/2005 | Lesser et al. |
| 6,889,091 B2 | 5/2005 | Hine et al. |
| 6,890,303 B2 | 5/2005 | Fitz |
| 6,898,464 B2 | 5/2005 | Edell et al. |
| 6,911,004 B2 | 6/2005 | Kim et al. |
| 6,911,496 B2 | 6/2005 | Rhee et al. |
| 6,920,359 B2 | 7/2005 | Meadows et al. |
| 6,921,413 B2 | 7/2005 | Mahadevan-Jansen et al. |
| 6,925,357 B2 | 8/2005 | Wang et al. |
| 6,929,636 B1 | 8/2005 | Von Alten |
| 6,936,003 B2 | 8/2005 | Iddan |
| 6,939,290 B2 | 9/2005 | Iddan |
| 6,939,376 B2 | 9/2005 | Shulze et al. |
| 6,950,707 B2 | 9/2005 | Whitehurst |
| 6,953,589 B1 | 10/2005 | Trautman et al. |
| 6,958,034 B2 | 10/2005 | Iddan |
| 6,959,215 B2 | 10/2005 | Gliner et al. |
| 6,960,227 B2 | 11/2005 | Jones et al. |
| 6,963,792 B1 | 11/2005 | Green |
| 6,991,617 B2 | 1/2006 | Hektner et al. |
| 7,003,352 B1 | 2/2006 | Whitehurst |
| 7,013,177 B1 | 3/2006 | Whitehurst et al. |
| 7,037,343 B2 | 5/2006 | Imran |
| 7,042,184 B2 | 5/2006 | Oleynikov et al. |
| 7,066,180 B2 | 6/2006 | Aylsworth et al. |
| 7,101,386 B2 | 9/2006 | Dobak, III |
| 7,115,109 B2 | 10/2006 | Gerdts et al. |
| 7,131,979 B2 | 11/2006 | DiCarlo et al. |
| 7,160,258 B2 | 1/2007 | Imran et al. |
| 7,181,261 B2 | 2/2007 | Silver et al. |
| 7,228,162 B2 | 6/2007 | Ward et al. |
| 7,236,821 B2 | 6/2007 | Cates et al. |
| 7,245,954 B2 | 7/2007 | Glukhovsky |
| 7,297,113 B1 | 11/2007 | Russell et al. |
| 7,341,577 B2 | 3/2008 | Gill |
| 7,365,509 B2 | 4/2008 | Park et al. |
| 7,383,071 B1 | 6/2008 | Russell et al. |
| 7,572,228 B2 | 8/2009 | Wolinsky et al. |
| 7,713,196 B2 | 5/2010 | Baker, Jr. |
| 7,744,542 B2 | 6/2010 | Piaget et al. |
| 7,801,626 B2 | 9/2010 | Moser |
| 7,840,271 B2 | 11/2010 | Kieval et al. |
| 7,857,767 B2 | 12/2010 | Ferren et al. |
| 2001/0029348 A1 | 10/2001 | Willis |
| 2001/0051766 A1 | 12/2001 | Gazdzinski |
| 2002/0065509 A1 | 5/2002 | Lebel et al. |
| 2002/0068080 A1 | 6/2002 | Lerner |
| 2002/0090388 A1 | 7/2002 | Humes et al. |
| 2002/0116029 A1 | 8/2002 | Miller et al. |
| 2002/0116034 A1 | 8/2002 | Miller et al. |
| 2002/0120263 A1 | 8/2002 | Brown et al. |
| 2002/0147480 A1 | 10/2002 | Mamayek |
| 2002/0156462 A1 | 10/2002 | Stultz |
| 2002/0165592 A1 | 11/2002 | Glukhovsky et al. |
| 2002/0169436 A1 | 11/2002 | Gurm et al. |
| 2002/0183721 A1 * | 12/2002 | Santini et al. ............... 604/890.1 |
| 2002/0188323 A1 | 12/2002 | Penner et al. |
| 2002/0193679 A1 | 12/2002 | Malave et al. |
| 2002/0193874 A1 | 12/2002 | Crowley |
| 2002/0198470 A1 | 12/2002 | Imran et al. |
| 2002/0198521 A1 | 12/2002 | Maguire |
| 2002/0198604 A1 | 12/2002 | Schulman et al. |
| 2003/0004403 A1 | 1/2003 | Drinan et al. |
| 2003/0023150 A1 | 1/2003 | Yokoi et al. |
| 2003/0024534 A1 | 2/2003 | Silvestri et al. |
| 2003/0040704 A1 | 2/2003 | Dorros et al. |
| 2003/0060723 A1 | 3/2003 | Joo et al. |
| 2003/0065358 A1 | 4/2003 | Frecker et al. |
| 2003/0069475 A1 | 4/2003 | Banik et al. |
| 2003/0069523 A1 | 4/2003 | Williams et al. |
| 2003/0151524 A1 | 8/2003 | Clark |
| 2003/0152823 A1 | 8/2003 | Heller |
| 2003/0158584 A1 | 8/2003 | Cates et al. |
| 2003/0163177 A1 | 8/2003 | Eggers et al. |
| 2003/0167000 A1 | 9/2003 | Mullick et al. |
| 2003/0214579 A1 | 11/2003 | Iddan |
| 2003/0220556 A1 | 11/2003 | Porat et al. |
| 2004/0008853 A1 | 1/2004 | Pelrine et al. |
| 2004/0018508 A1 | 1/2004 | Friedman |
| 2004/0019374 A1 | 1/2004 | Hojeibane et al. |
| 2004/0034332 A1 | 2/2004 | Uhland |
| 2004/0064093 A1 | 4/2004 | Hektner et al. |
| 2004/0073177 A1 | 4/2004 | Hickle |
| 2004/0073190 A1 | 4/2004 | Deem et al. |
| 2004/0092825 A1 | 5/2004 | Madar et al. |
| 2004/0097805 A1 | 5/2004 | Verard et al. |
| 2004/0097819 A1 | 5/2004 | Duarte |
| 2004/0098030 A1 | 5/2004 | Makower et al. |
| 2004/0133147 A1 | 7/2004 | Woo |
| 2004/0138517 A1 | 7/2004 | Osario et al. |
| 2004/0147939 A1 | 7/2004 | Rabkin et al. |
| 2004/0148034 A1 | 7/2004 | Kagan et al. |
| 2004/0162469 A1 | 8/2004 | Imran |
| 2004/0162501 A1 | 8/2004 | Imran |
| 2004/0176664 A1 | 9/2004 | Iddan |
| 2004/0199246 A1 | 10/2004 | Chu et al. |
| 2004/0225325 A1 | 11/2004 | Bonutti |
| 2004/0225326 A1 | 11/2004 | Weiner et al. |
| 2004/0260391 A1 | 12/2004 | Santini, Jr. et al. |
| 2004/0267240 A1 | 12/2004 | Gross et al. |
| 2005/0004553 A1 | 1/2005 | Douk |
| 2005/0021023 A1 | 1/2005 | Guglielmi et al. |
| 2005/0027236 A1 | 2/2005 | Douk |
| 2005/0058701 A1 | 3/2005 | Gross et al. |
| 2005/0065592 A1 | 3/2005 | Holzer |
| 2005/0069925 A1 | 3/2005 | Ford et al. |
| 2005/0079132 A1 | 4/2005 | Wang et al. |
| 2005/0107870 A1 | 5/2005 | Wang et al. |
| 2005/0113460 A1 | 5/2005 | Glick |
| 2005/0121411 A1 | 6/2005 | Cohen |
| 2005/0126916 A1 | 6/2005 | Lockard et al. |
| 2005/0149170 A1 | 7/2005 | Tassel et al. |
| 2005/0151524 A1 | 7/2005 | Sae-Ueng et al. |
| 2005/0177223 A1 | 8/2005 | Palmaz |
| 2005/0182482 A1 | 8/2005 | Wang et al. |
| 2005/0203613 A1 | 9/2005 | Arney et al. |
| 2005/0216074 A1 | 9/2005 | Sahatjian et al. |
| 2005/0221529 A1 | 10/2005 | Bang et al. |
| 2005/0228259 A1 | 10/2005 | Glukhovsky et al. |
| 2005/0234393 A1 | 10/2005 | Wood, Jr. |
| 2005/0234440 A1 | 10/2005 | Wood, Jr. |
| 2005/0238689 A1 | 10/2005 | Carpenter et al. |
| 2005/0272806 A1 | 12/2005 | Falotico et al. |
| 2005/0272974 A1 | 12/2005 | Iddan |
| 2005/0277839 A1 | 12/2005 | Alderman et al. |
| 2005/0278020 A1 | 12/2005 | Wang et al. |
| 2006/0004395 A1 | 1/2006 | Chiel et al. |
| 2006/0009810 A1 | 1/2006 | Mann et al. |
| 2006/0015146 A1 | 1/2006 | Girouard et al. |
| 2006/0037617 A1 | 2/2006 | Walke et al. |
| 2006/0042631 A1 | 3/2006 | Martin et al. |
| 2006/0074479 A1 | 4/2006 | Bailey et al. |
| 2006/0119304 A1 | 6/2006 | Farritor et al. |
| 2006/0167339 A1 | 7/2006 | Gilad et al. |
| 2007/0010868 A1 | 1/2007 | Ferren et al. |
| 2007/0066929 A1 | 3/2007 | Ferren et al. |
| 2007/0088334 A1 | 4/2007 | Hillis et al. |
| 2007/0225634 A1 | 9/2007 | Ferren et al. |
| 2008/0063703 A1 | 3/2008 | Gross et al. |
| 2008/0066929 A1 | 3/2008 | Costa et al. |
| 2008/0103440 A1 | 5/2008 | Ferren et al. |
| 2008/0243056 A1 | 10/2008 | Hillis et al. |

OTHER PUBLICATIONS

Korean Intellectual Property Office (KIPO); Notice of Office Action; App. No. 10-2007-7009231; Jun. 8, 2012; pp. 1-5 (translation provided, 2 psges).

* cited by examiner

SYSTEM WITH A RESERVOIR FOR PERFUSION MANAGEMENT

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed applications; the present application also claims the earliest available effective filing date(s) from, and also incorporates by reference in its entirety all subject matter of any and all parent, grandparent, great-grandparent, etc. applications of the following listed applications:

1. For purposes of the USPTO extra-statutory requirements, the present application constitutes a continuation of U.S. patent application Ser. No. 10/827,576 entitled A SYSTEM FOR PERFUSION MANAGEMENT, naming Lowell L. Wood Jr. as inventor, filed Apr. 19, 2004, which is currently co-pending, or is an application of which a currently co-pending application is entitled to the benefit of the filing date.
2. For purposes of the USPTO extra-statutory requirements, the present application constitutes a continuation of U.S. patent application Ser. No. 10/827,578 entitled A SYSTEM WITH A SENSOR FOR PERFUSION MANAGEMENT, naming Lowell L. Wood Jr. as inventor, filed Apr. 19, 2004, which is currently co-pending, or is an application of which a currently co-pending application is entitled to the benefit of the filing date.
3. For purposes of the USPTO extra-statutory requirements, the present application constitutes a continuation of U.S. patent application Ser. No. 10/827,390 entitled A TELESCOPING PERFUSION MANAGEMENT SYSTEM, naming Lowell L. Wood, Jr. as inventor, filed Apr. 19, 2004, which is currently co-pending, or is an application of which a currently co-pending application is entitled to the benefit of the filing date.
4. For purposes of the USPTO extra-statutory requirements, the present application constitutes a continuation of U.S. patent application Ser. No. 10/827,572 entitled SYSTEM WITH A RESERVOIR FOR PERFUSION MANAGEMENT, naming Lowell L. Wood, Jr. as inventor, filed Apr. 19, 2004, now U.S. Pat. No. 7,850,676 which is currently co-pending, or is an application of which a currently co-pending application is entitled to the benefit of the filing date.
5. For purposes of the USPTO extra-statutory requirements, the present application constitutes a continuation of U.S. patent application Ser. No. 11/891,371 entitled A TELESCOPING PERFUSION MANAGEMENT SYSTEM, naming Lowell L. Wood Jr. as inventor, filed Aug. 9, 2007, which is currently co-pending, or is an application of which a currently co-pending application is entitled to the benefit of the filing date.
6. For purposes of the USPTO extra-statutory requirements, the present application constitutes a continuation of U.S. patent application Ser. No. 11/891,573 entitled A TELESCOPING PERFUSION MANAGEMENT SYSTEM, naming Lowell L. Wood Jr. as inventor, filed Aug. 9, 2007, which is currently co-pending, or is an application of which a currently co-pending application is entitled to the benefit of the filing date.
7. For purposes of the USPTO extra-statutory requirements, the present application constitutes a continuation of U.S. patent application Ser. No. 11/891,355 entitled A SYSTEM WITH A RESERVOIR FOR PERFUSION MANAGEMENT, naming Lowell L. Wood Jr. as inventor, filed Aug. 9, 2007, which is currently co-pending, or is an application of which a currently co-pending application is entitled to the benefit of the filing date, and which issues as U.S. Pat. No. 7,871,402 on Jan. 18, 2011.
8. For purposes of the USPTO extra-statutory requirements, the present application constitutes a continuation of U.S. patent application Ser. No. 11/891,333 entitled A SYSTEM WITH A RESERVOIR FOR PERFUSION MANAGEMENT, naming Lowell L. Wood Jr. as inventor, filed Aug. 9, 2007, which is currently co-pending, or is an application of which a currently co-pending application is entitled to the benefit of the filing date, and which issues as U.S. Pat. No. 7,867,217 on Jan. 11, 2011.
9. For purposes of the USPTO extra-statutory requirements, the present application constitutes a continuation of U.S. patent application Ser. No. 11/891,334 entitled A SYSTEM FOR PERFUSION MANAGEMENT, naming Lowell L. Wood Jr. as inventor, filed Aug. 9, 2007, which is currently co-pending, or is an application of which a currently co-pending application is entitled to the benefit of the filing date.
10. For purposes of the USPTO extra-statutory requirements, the present application constitutes a continuation of U.S. patent application Ser. No. 11/891,356 entitled A SYSTEM FOR PERFUSION MANAGEMENT, naming Lowell L. Wood Jr. as inventor, filed Aug. 9, 2007, now U.S. Pat. No. 7,879,023 which is currently co-pending, or is an application of which a currently co-pending application is entitled to the benefit of the filing date.
11. For purposes of the USPT extra-statutory requirements, the present application constitutes a continuation of U.S. patent application Ser. No. 11/891,355 entitled A SYSTEM WITH A RESERVOIR FOR PERFUSION MANAGEMENT, naming Lowell L. Wood Jr. as inventor, filed Aug. 9, 2007, now U.S. Pat. No. 7,871,402 which is currently co-pending, or is an application of which a currently co-pending application is entitled to the benefit of the filing date.

TECHNICAL FIELD

The present application relates, in general, to detection and/or treatment.

SUMMARY

In one aspect, a system includes but is not limited to: a body portion; at least one extensible finger coupled to said body portion; at least one reservoir in communication with said extensible finger; and a control circuitry coupled to said extensible finger, or said body portion. In addition to the foregoing, other system aspects are described in the claims, drawings, and text forming a part of the present application.

In one aspect, a method includes but is not limited to: fabricating a device by forming a cavity for storing a receivable; coupling a flexible conduit to said cavity, the conduit being configured to extend from said cavity to a target location in an animal's body; and coupling said flexible conduit and said cavity to a monitoring system, said monitoring system including logic or software configured for directing said receivable from said cavity to said target location. In addition to the foregoing, other method aspects are described in the claims, drawings, and text forming a part of the present application.

In another aspect, a method includes but is not limited to: storing a receivable in an implanted storage medium; extending a flexible conduit between said storage medium and a target location; and transmitting said receivable from said storage medium to said target location. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other method and or system aspects are set forth and described in the text (e.g., claims and/or detailed description) and/or drawings of the present application.

The foregoing is a summary and thus contains, by necessity; simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE FIGURES

The use of the same symbols in different drawings typically indicates similar or identical items.

DETAILED DESCRIPTION

The present application uses formal outline headings for clarity of presentation. However, it is to be understood that the outline headings are for presentation purposes, and that different types of subject matter may be discussed throughout the application (e.g., device(s)/structure(s) may be described under the process(es)/operations heading(s) and/or process(es)/operations may be discussed under structure(s)/process(es) headings). Hence, the use of the formal outline headings is not intended to be in any way limiting.

1. Perfusion Management Device(s) and/or Process(es).

Figure 1:
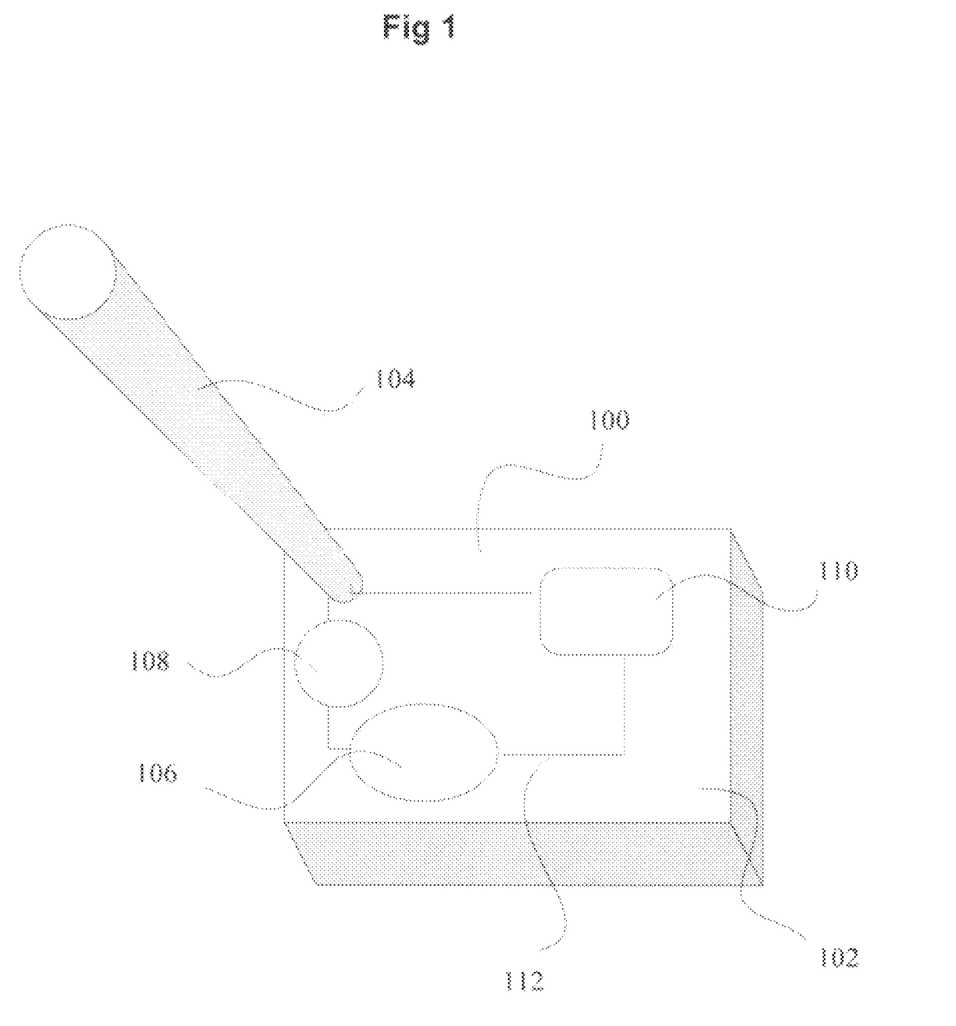
FIG. 1 is a front-plan view of a device for perfusion management 100.

With reference now to FIG. 1, shown is a front plan view illustrative of various exemplary perfusion management device(s) and/or process(es). Accordingly, the present application first describes certain specific exemplary structures of FIG. 1; thereafter, the present application illustrates certain specific exemplary processes. Those having skill in the art will appreciate that the specific devices and processes described herein are intended as merely illustrative of their more general counterparts.

A. Structure(s) and or Device(s)

With reference to the figures, and with reference now to FIG. 1, shown is a front-plan view of a device for perfusion management 100. The device for perfusion management 100 includes a body portion 102 from which at least one extensible finger 104 projects. At least one reservoir 106 within the body portion 102 contains a fluid, for example, a fluid for treatment. A controllable valve 108 provides a path through which the fluid may travel to the at least one extensible finger 104. A control circuit 110 provides a control signal that may open or close the control valve 108.

Figure 2:
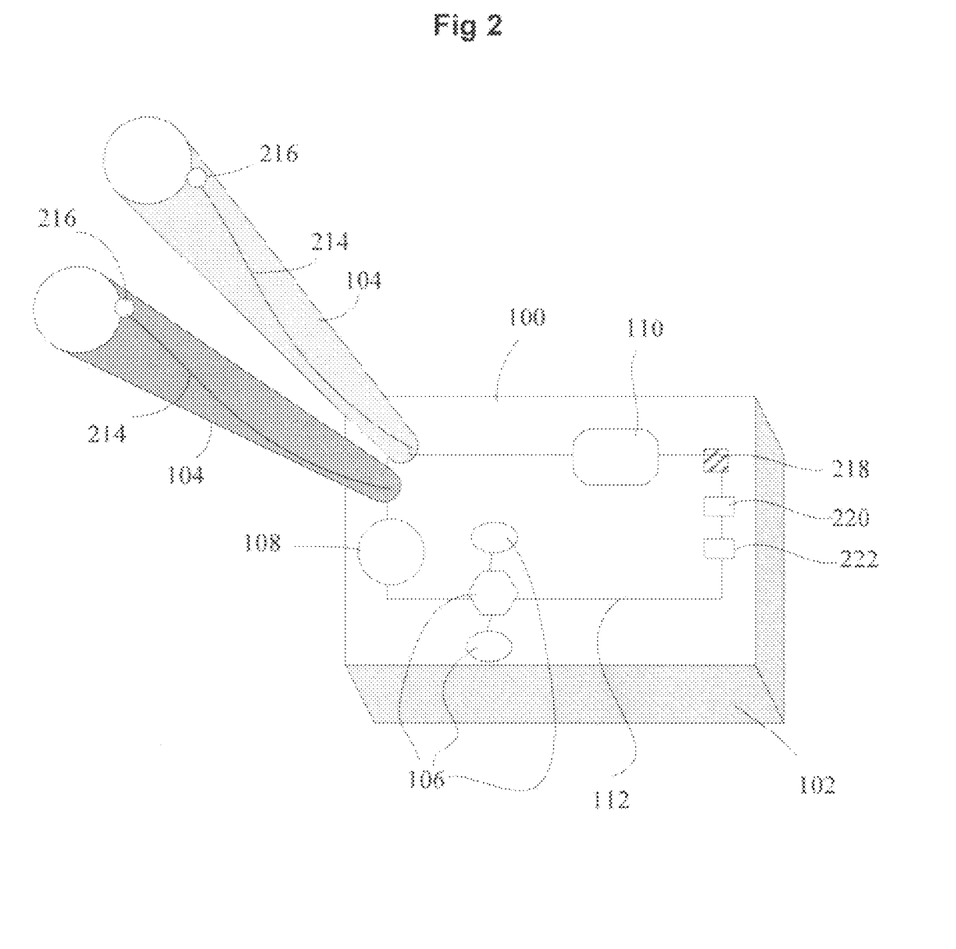
FIG. 2 is a front-plan view of another aspect of the device for perfusion management 100.

Referring now to FIG. 2, depicted is an aspect of the device for perfusion management 100 which includes a body portion 102 from which a set of extensible fingers projects. In one aspect, at least one of the extensible finger 104 of the set of extensible fingers has a sensor 216 at the distal end of the at least one of the extensible finger 104. Additionally, a sense line 214 connects the control circuit 110 to the sensor 216 at the distal end of the extensible finger 104. The control circuit 110 may be connected to a sense line 214 that allows it to monitor the fluid levels within the at least one reservoir 106.

Continuing to refer to FIG. 2, in one aspect, each of the extensible finger 104 of the set of extensible fingers is in fluid communication with at least one of a respective reservoir 106 filled with a different fluid for delivery. In another approach, the at least one reservoir 106 may be coupled to a mixing chamber where the fluid contents of the at least one reservoir 106 are present for mixing and the mixed contents enter the extensible finger 104 for delivery to a selected location. The choice of the fluid in the at least one reservoir 106 may depend, for example, on the purpose of the device, for example, treatment of colon cancer, treatment of breast cancer, or treatment of an arterial disease. The choice of fluid in the reservoir 106 includes, but is not limited to, for example, a chemical, a chemical compound, a protein, a lipoprotein, a glycoprotein, a sugar, a lipid, an antigen, an antibody, a cytokine, a peptide, a neurotransmitter, a hormone, an ion, a messenger a molecule, a nucleic acid, an engineered nucleic acid, a nucleic acid vector, a drug, a cell, a cell fragment, a cell organelle, a liposome, a pharmaceutical agent, a biological material, or a biological fraction. The reservoir 106 may also be utilized for storage and disposal of operational fluids. Also, although the exemplary embodiment described herein focuses primarily on fluid delivery, one skilled in the art will understand that fluid-like substances, such as gels, and fluidizable substances or non-fluid type substances, such as small solid particles, may be delivered in accordance with the invention. It will also be appreciated by those having skill in the art that the nature of the fluid in the reservoir 206 includes, for example, and is not limited to, a liquid, a solution, a mixture, a gel, a colloid, a colloid of a suitable viscosity, a suspension, an emulsion, or any material of low shear-strength for delivery to a site.

In one aspect one or more fluids are delivered to one or more of selected locations by the device for perfusion management 100. The selected location may be, for example, in proximity to or within a tumor, a circulatory system, an aorta, a vena cava, a site of therapy, or a site of investigation in an animal.

Continuing to refer to FIG. 2, a pump 218 provides fluid at a controlled flow rate for delivery to a site from the reservoir 106. It will be appreciated by those skilled in the art that the type of pump is not critical to the invention and may include, for example, a mechanical pump, a piezoelectric pump, an osmotic pump, a source of pressure, or a device for maintaining a positive flow of fluid through the device. Additionally, fluid flow may be further modulated with micro valves and self-pressurizing fluidic reservoirs. Moreover, in some applications, the fluid may be delivered without a pump. For example, fluid delivery may be controlled using a pressurized bladder, controlled dissolution or dilution of a material, a drip or gravity type of approach, or any other suitable approach to deliver the appropriate amount or an appropriate delivery-rate of the fluid.

Figures 3A, 3B, 3C:
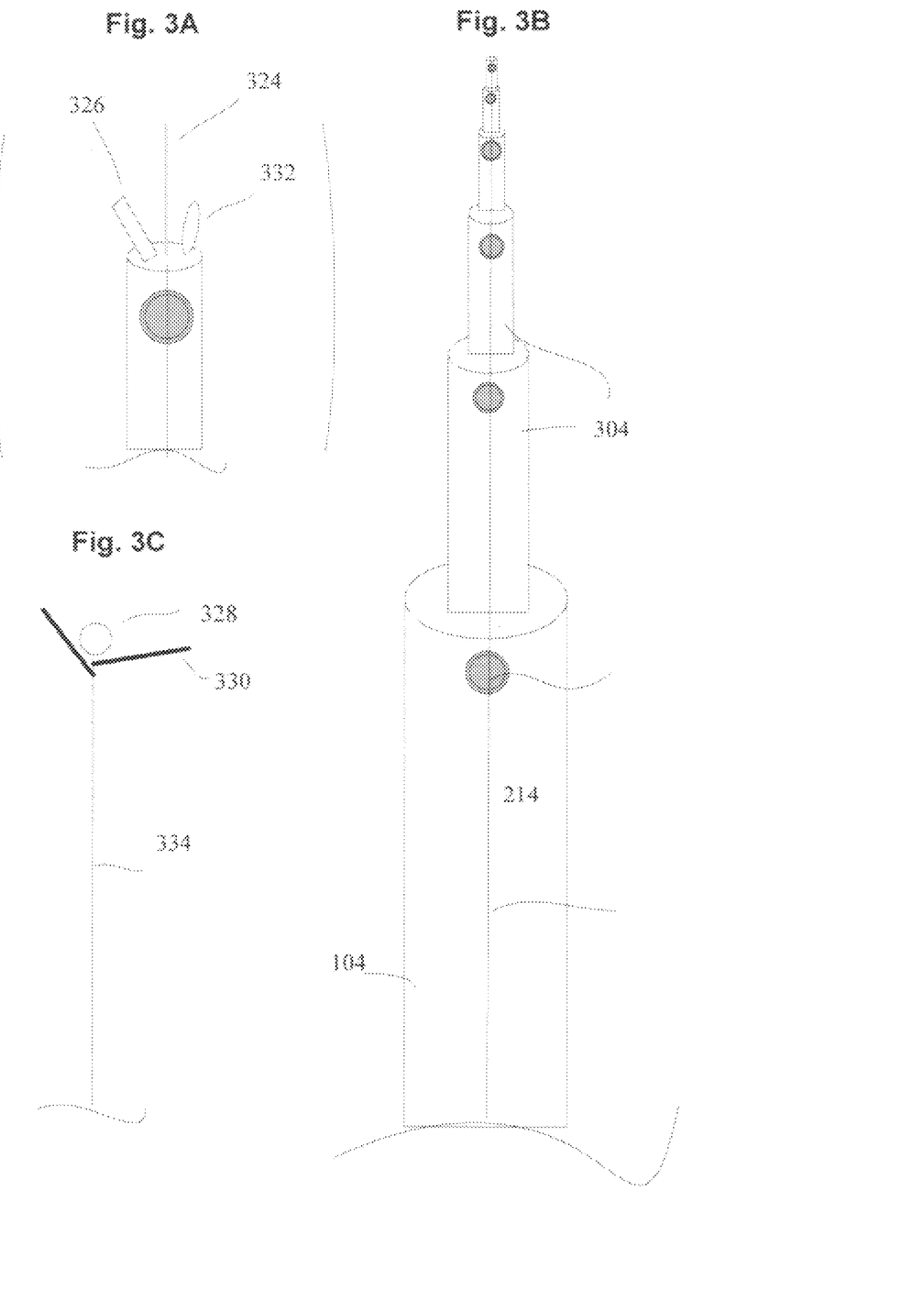
FIGS. 3A, 3B, and 3C show exploded views of various aspects an extensible finger 104 of the device of FIG. 1.

With reference now to FIGS. 3A, 3B, and 3C, show exploded views of various aspects of the extensible finger 104 showing a plurality of telescoping segments 304 with the sensor 216 at the distal end of each of the telescoping segments 304. In one aspect of the invention, the sensor 216 is an array of sensors, deployed from one or more portholes, at the distal end of each of the telescoping segments 304. In one approach, the portholes are sized and shaped to provide access through which the sensors 216 may be deployed. The portholes may include seals, stress relief or other features appropriate for proper mechanical deployment. In one approach, one or more of the portholes can be controllably opened or closed to provide communication exterior to the extensible finger or main body. The sensor 216 may be retracted within the port hole and deployed through the porthole. Where the porthole can be opened and closed, the porthole can close to limit communication and can be opened for deployment. The array of sensors may include, but is not limited to, for example, sensors for detecting pressure, temperature, chemical, gas, electrolyte, flow, volume, composition, or concentration. In an alternate aspect of the invention, microelectrodes, such as, for example, solid-state microelectrodes are sensitized with an agent for detecting a relevant interactor. Examples of the agent include, but are not limited to, for example, agonists of angiogenesis. The choice of sensor 216 depends on the physiological variable being monitored, treated, or controlled. The term "physiological variable" refers to any and all measurements relating to the functioning of a living organism under normal, sub-normal, or abnormal states.

Figure 4:
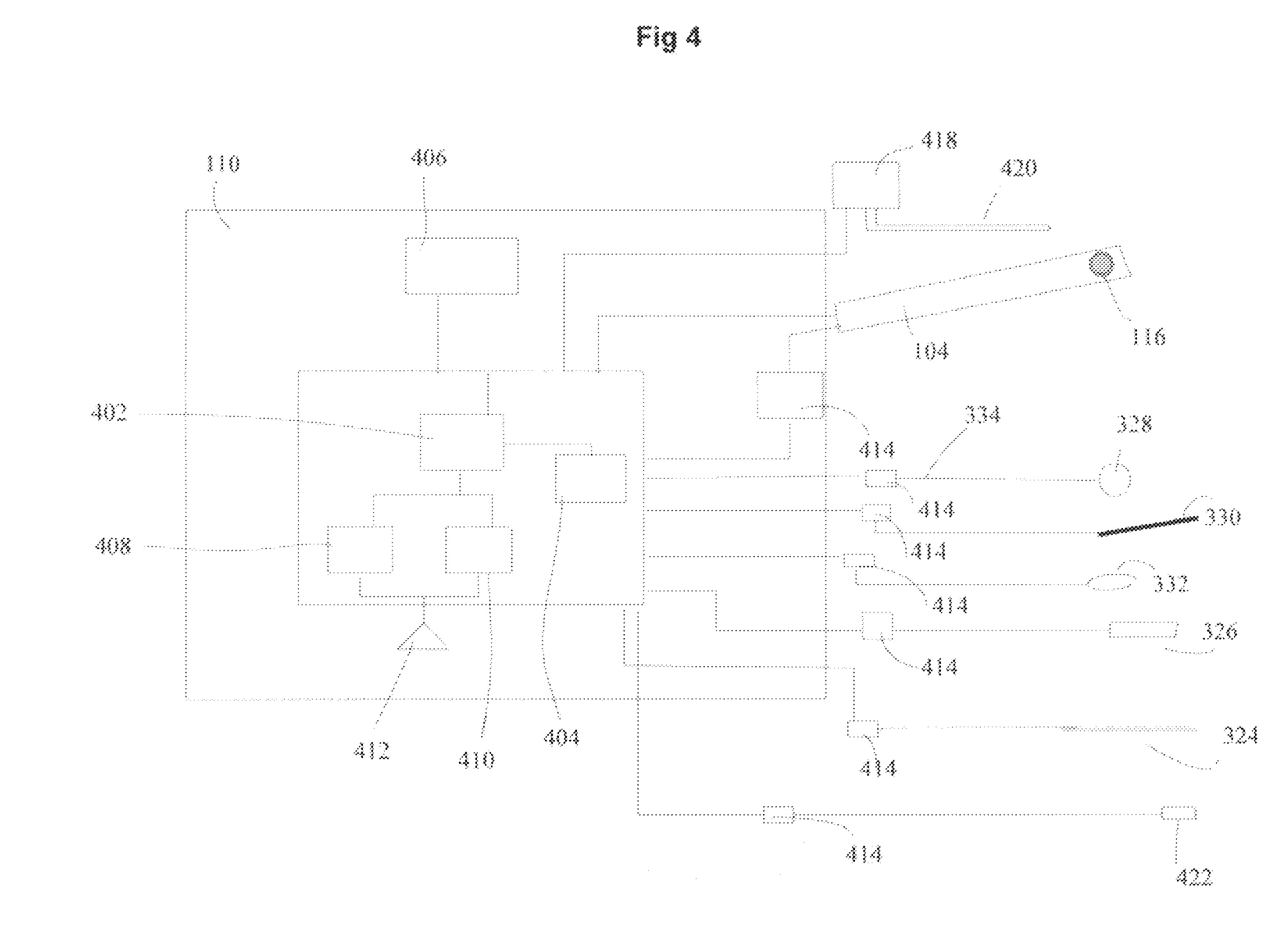
FIG. 4 is a schematic view of the control circuit 110 and devices in communication with the control circuit 110.

Continuing to refer to FIGS. 3A, 3B, 3C, and referring now to FIG. 4, an operative tool 324 is coupled to the distal most telescoping segment 304, or deployed from the porthole, or carried by the extensible finger 104, further including a carrying line 334 in communication with the control circuit 110. The operative tool 324 includes, but is not limited to, for example, one or more of a combination of, a tool positioner, an ablation device, a laser, a vacuum, a siphon 326, an evacuation device, a fluid dispenser 328, a cauterizer 330, a stent 332, a tissue-liquefying device, or a source of an electric or an electromagnetic charge 422. The vacuum or the siphon is employed for removing a cell, a mass of cells, a tissue, a fluid, a gel, a sample, a debris, a contaminant, or other material for which removal is desired or appropriate. The ablation device operates for perturbing or reducing the structural integrity or viability of a cell, a mass of cells, an assembly of biological materials exhibiting shear strength, or a tissue. The assembly of biological materials includes, for example, blood clots, cartilage, or bone. The source of an electric or electromagnetic charge 422 includes, but is not limited to, for example, steady state electric currents, time-varying electric currents, alternating electric currents, radio waves, microwaves, ultraviolet rays, infra-red rays, optical rays, terahertz beams, and the like.

Continuing to refer to FIGS. 3A, 3B, and 3C, it will be appreciated by those having skill in the art that the operative tool 324 may include a set of devices having general or "multi-purpose" utility. The operative tool 324 may include, but is not limited to, for example, a combination of the fluid dispenser 328, the siphon 326, and the ablation device. In this example the operative tool combination, for example, delivers the fluid or gel, ablates cells, and removes debris.

Continuing to refer to FIGS. 3A, 3B, and 3C, the plurality of telescoping segments 304 may themselves be hollow forming a conduit for delivery of the fluid to a site, or for housing a circuitry coupling the control circuit 110 to the operative tool 324, or for housing a mechanism that guides the arm 104 or the plurality of telescoping segments 304.

With reference now to FIG. 4, illustrated is a schematic view of the control circuit 110 and devices in communication with the control circuit 110. The device for perfusion management 100 shows a data transmitter 410, and a data receiver 408 coupled to the control circuit 110. An antenna 412 may be used for transmitting data to the exterior wirelessly. The antenna 412 is shown diagrammatically, but may be a structure, such as a strip antenna, that may be integrated in a manner that does not impair or significantly perturb system performance. The control circuit 110 is depicted as having a processor 402 coupled to a memory 404 that provides data storage and retrieval capability, and a power source 406. Feedback circuitry or logic circuitry provides communication between the control circuit 110 and devices in communication with it. In some applications, a software program providing instructions may be stored in the memory 404 to control operation of the control circuitry or to store data gathered under control of the control circuitry. Additionally, the control circuit 110 may have components for system integrated digital data gathering, processing, storage, compression and transmission. These can provide data control capabilities and operation control capabilities. For example, the transmission components may communicate through the antenna 412 to a person, system, computer, or device exterior to the body. This communication can allow data gathered by the sensors to be displayed, stored or otherwise processed in the external environment. Additionally, this communication may allow for the processed data or a plurality of new data to be received from the exterior by the device for perfusion management 100. Data compression can allow the control circuitry to store data representing larger amounts of data to be stored in the memory 404 or to be transmitted to the exterior environment in a more efficient manner.

Continuing to refer to FIG. 4, one or more of the operative tools 324 are mounted on an actuator 414 which allows for the independent movement of each tool. Alternatively, one or more operative tools 324 may be mounted as a unit on one actuator 414 and moved as a group, for example, forming an aspirating-dispensing unit. For example, the fluid dispenser 328 and the siphon 326 may be mounted together as a group. The actuator 414 may be a motor, a piezo electrically driven actuator, a micromechanical or electrical effector, or the like.

Continuing to refer to FIG. 4, the extensible finger 104 may include an imaging device deployed from the porthole or from the distal end of the extensible finger 104 or carried by a carrying line 334. The term "imaging device" being used herein to designate in general those components, circuits, assemblies and sub-assemblies comprising electrical, optical, or opto-electronic components. In one aspect, the control circuit 110 is coupled to the imaging device that includes a laser 418, or a source of light or scene-illuminating radiation, coupled to an optical feed line 420 to illuminate an area. A charge coupled device is positioned to capture data from the illuminated area and provides an electronic signal indicative of the area imaged. Conventional circuitry then produces a digital representation that may be displayed, stored in the memory 404, or otherwise processed. The displayed image may serve, for example, for guiding the extensible finger 104 to the selected location or for determining the efficacy of a treatment or a procedure. One skilled in the art will recognize that the imaging device described herein is exemplary of imaging devices and that other imaging devices, including for example, raster and line-scanning imagers, nonvisible spectral imagers, and fluorescence imagers, may be included.

Figure 5:
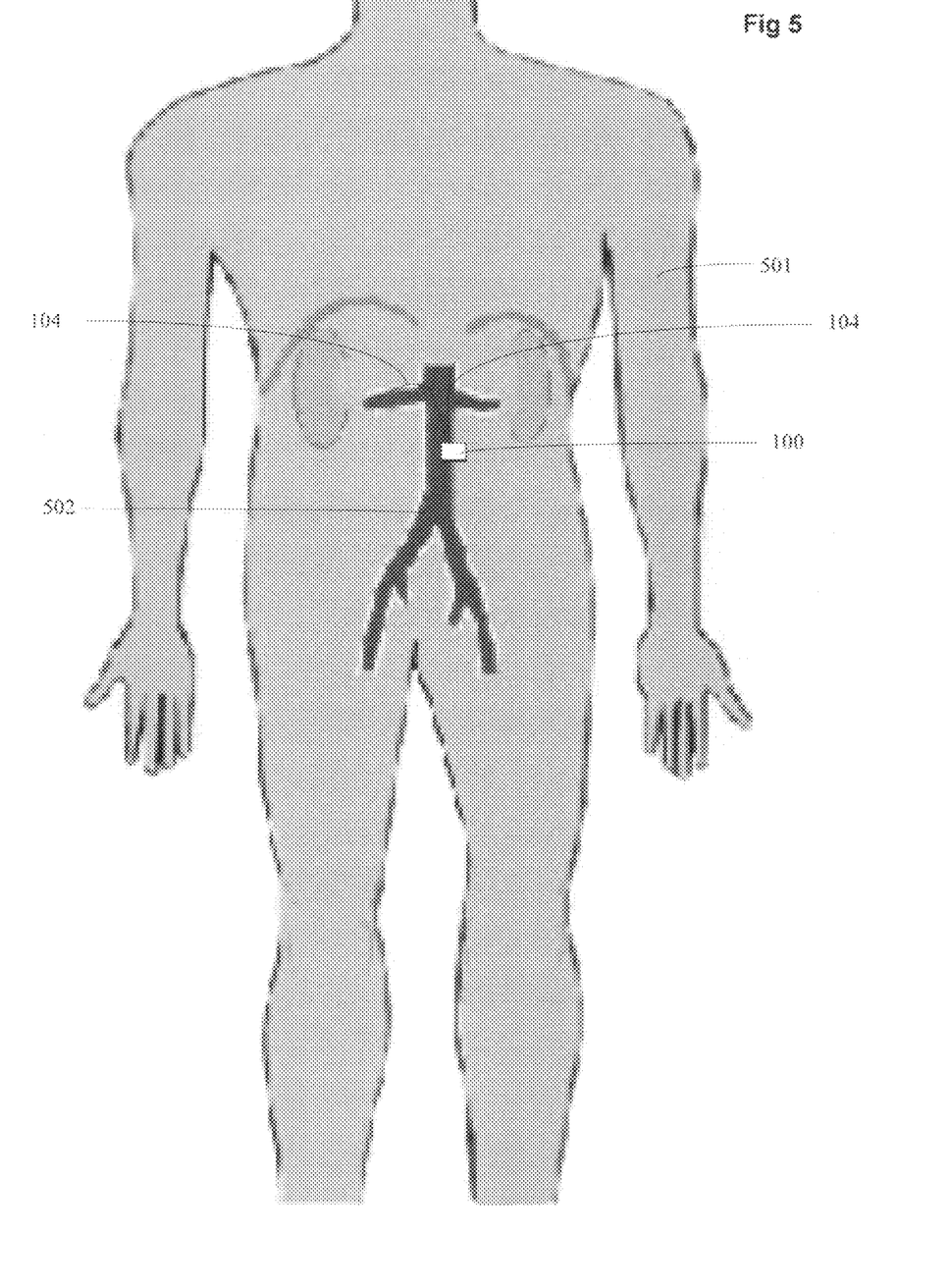
FIG. 5 illustrates an example wherein the device for perfusion management 100 is placed in a selected location in a human body 501.

With reference now to FIG. 5, the device for perfusion management 100 is depicted implanted in an aorta 502 with the extensible finger 104 traveling a blood vessel in a human body 501. Additionally, the device for perfusion management 100 is configured for full or partial placement in the human body 501. The configuration may incorporate a combination of the following criteria, including but not limited to, dimensions, composition, shape, power dissipation level, or texture. In one aspect, the body portion 102 is sized for implantation in proximity to the aorta 502 or the vena cava and the extensible finger 104 is sized for traveling a blood vessel in an animal, for example, the human body 501. In this aspect, if the vasculature decreases two-fold, each of the telescoping segments 304 has about a two-fold decrease in diameter. The length of the extensible finger 104, for example, depends upon the distance between the selected location and the location of the body portion 102, and the route traveled by the extensible finger 104 to arrive at the selected location. It will be appreciated by those having skill in the art that the extensible finger 104 including the one or more of the operative tools 324 is of a size, dimension or shape operable for traveling one or more blood vessel of decreasing or increasing luminal diameter. It will also be appreciated by those having skill in the art that the extensible finger 104 and the one or more operative tool 324 may pass through the wall of the lumen, or trans-luminally, to the surrounding tissue for detecting, delivery of a treatment, or for sampling. It will also be appreciated by those having skill in the art that the trans-luminal mode described is not limited to blood vessels and includes the space or cavity of an organ or structure.

It will also be appreciated by those having skill in the art that the device for perfusion management 100 and its components, such as, for example, the extensible finger 104, the plurality of telescoping segments 304, or one or more operative tools 324, has a size, dimension, shape, material, and properties of flexion, retraction, and extension to allow for the steering, guiding, or positioning of the components of the device for perfusion management 100. For example, the extensible finger 104 may need to be steered around an occlusion or a fork in the vasculature. In this example, the extensible finger 104 may need to retracted, repositioned and then extended in a new direction. Extending, retracting or repositioning of the extensible finger 104 may be accomplished by techniques known in the art, for example, by using a guide wire or a by employing a shape polymer. In another aspect, the extensible finger may be retracted and then "punched through" an occlusion to dislodge it. In this example, lasers, shears, or a drug may be employed to degrade the occlusion. In this example, subsequent to the dislodgement and degradation of the occlusion, the siphon 326 or an evacuation device is employed to evacuate any debris, before the extensible finger 104 continues traveling the circulatory system. It will also be appreciated by those skilled in the art that the device for perfusion management 100 is not restricted to traveling the circulatory system but may be implanted in any tissue, such as, for example, nerve, epithelial, dermal, subdermal, connective, or muscle tissue. Additionally, the device for perfusion management 100 may be implanted in inter-tissue spaces, or inter-organ spaces, for example, those found within a body cavity.

In one aspect the device for perfusion management 100 includes an array of sensors 116 positioned across the plurality of telescoping segments 304 for monitoring, tracking, or mapping a gradient of temperature, pressure, flow, or material concentration in one or more locations. The one or more location may be, for example, a tissue, an artery, or a vein. In another aspect the device for perfusion management 100 has an auto-correct feature for correcting a sub-normal or abnormal gradient of temperature, pressure, flow concentration, or material concentration The device for perfusion management 100 may be composed of materials known in the art, for example, a metal, a ceramic, a glass, a plastic, a polymer, a biologically compatible material, or a combination. For example, the device for perfusion management 100 may be made of helically-coiled stainless steel wire and coated with a polymer, such as, Teflon™. In another example, the device for perfusion management 100 may be made of helically-coiled stainless steel wire and coated with a polymer and impregnated with one or more of a biological material, for example, including but not limited to, anti coagulants, or inhibitors.

B. Operation(s) and/or Process(es)

Those having skill in the art will appreciate that some or all of the components of the device for perfusion management 100 may be present ex-vivo. In one implementation, the device for perfusion management 100 is placed in proximity to the location on the animal, for example, the human body 501, and the extensible finger 104 directed to the selected location and an effective agent delivered in proximity to the selected location. The extensible finger 104 may be retracted after such a delivery, leaving the device for perfusion management 100 in place at the location, until time for a future delivery of the effective agent or another operation. In this implementation, the majority of the device for perfusion management 100 is ex vivo while the extensible finger 104 alternates between ex vivo and in vivo states.

In another aspect, some or all the components of the device for perfusion management 100 are present in vivo. In one implementation, the device for perfusion management 100 is placed in proximity to the location within the animal, for example, the human body 501, and the extensible finger 104 directed to a selected location and an effective agent delivered in proximity to the selected location. The extensible finger 104 may be retracted after such a delivery, leaving the device for perfusion management 100 in place at the location, until time for a future delivery or another operation. In this implementation, the majority of the device for perfusion management 100 is in-vivo while the extensible finger 104 alternates between retracted, partially retracted or unretracted states.

In one implementation, the device for perfusion management 100 is operable by a person. The person monitors, guides, positions, and performs other actions/operations or manages a response consistent with the device for perfusion management 100 being managed by the person. In such an implementation a separate display device can present imagery to aid the person. The imagery may be captured as described above with reference to FIG. 4, may be computer generated or may be captured by a separate imaging device internal to or external to the animal, for example, the human body 501. Actions may be performed under control of the person who may be on site or may be linked from a remote location, or the device for perfusion management 100 may be programmed to perform some or all functions automatically. For example, the device for perfusion management 100 may be programmed to perform functions, such as, lumen clearance, lumen maintenance, monitoring of concentrations, sending of alerts, delivery of one or more of the effective agent at timed intervals or locations, self-check, and self-diagnosis. It will be appreciated by those of skill in the art that the device for perfusion management 100 may be programmed for complete automatic operation of one or more functions.

C. Variation(s), and/or Implementation(s)

Those having skill in the art will recognize that the present application teaches modifications of the devices, structures, and/or processes within the spirit of the teaching herein. For example, the device for perfusion management 100 need not be limited to managing perfusion. The device provides a mechanism for exploring one or more regions and/or reaching a location within an animal, obtaining information, communicating this information, performing operations, performing procedures, and providing treatment. In another example, the device for perfusion management 100 may find utility in the management of physiological functions, the detection or elimination of pathological functions or conditions, and/or treatment of diseases of non-human animals. Other modifications of the subject matter herein will be appreciated by one of skill in the art in light of the teachings herein.

The foregoing described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined solely by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations), etc.

What is claimed is:

1. A system for perfusion management comprising:
    one or more conduits comprising a plurality of retractable segments configured to telescopically extend;
    circuitry configured for operating one or more actuators for delivering one or more receivables via the one or more conduits;
    a sensor array distributed along the one or more conduits; and
    circuitry configured for obtaining data using at least one sensor of the sensor array, the at least one sensor positioned at one or more controllably openable and closeable portholes of the one or more conduits.

2. The system of claim 1, wherein the one or more conduits include one or more flexible conduits.

3. The system of claim 1, wherein the one or more conduits include one or more guidable and/or movable conduits.

4. The system of claim 1, wherein the one or more conduits include at least one of programmably controllable, guidable, or positionable conduits.

5. The system of claim 1, wherein the one or more conduits include at least one of wirelessly controllable, guidable, or positionable conduits.

6. The system of claim 1, wherein the one or more conduits include one or more articulatable conduits.

7. The system of claim 1, wherein the one or more conduits including include one or more stent portions.

8. The system of claim 1, wherein the one or more conduits include one or more diameter varying conduits.

9. The system of claim 1, wherein the one or more receivables are delivered from one or more storage cavities via the one or more conduits.

10. The system of claim 1, wherein the one or more receivables include one or more fluid receivables.

11. The system of claim 1, wherein the one or more receivables are delivered from one or more mixing chambers via the one or more conduits.

12. The system of claim 1, wherein the one or more receivables are delivered from one or more remote sources via the one or more conduits.

13. The system of claim 1, wherein the one or more receivables are delivered via the one or more conduits at one or more controlled rates.

14. The system of claim 1, wherein the at least one sensor of a sensor array distributed along the one or more conduits obtains data including one or more variable gradient maps using at least one sensor positioned at one or more controllably openable and closable portholes of the one or more conduits.

15. The system of claim 1, further comprising:
    circuitry configured for receiving and/or transmitting data.

16. The system of claim 1, further comprising:
    circuitry configured for wirelessly receiving and/or transmitting data.

17. The system of claim 1, further comprising:
    circuitry configured to operate one or more actuators for performing one or more operations using one or more operative tools.

18. The system of claim 1, further comprising:
circuitry configured to operate the one or more actuators for performing one or more operations using one or more sources of pressure.

19. The system of claim 1, further comprising:
circuitry configured to operate the one or more actuators for performing one or more operations using one or more chargeable polymers.

20. The system of claim 1, further comprising:
circuitry configured to operate the one or more actuators for performing one or more operations using electric charge and/or radiation.

21. The system of claim 1, wherein the system is implantable.

* * * * *

UNITED STATES PATENT AND TRADEMARK OFFICE
CERTIFICATE OF CORRECTION

PATENT NO.          : 8,361,056 B2                                      Page 1 of 1
APPLICATION NO.     : 12/930916
DATED               : January 29, 2013
INVENTOR(S)         : Lowell L. Wood, Jr.

It is certified that error appears in the above-identified patent and that said Letters Patent is hereby corrected as shown below:

In the Claims:

Claim 14, Column 10, Line 54 please delete "of a sensor array distributed along the one or more conduits"

Claim 14, Column 10, Line 56 please amend "using at least one sensor positioned at one or more" and replace with --using the at least one sensor positioned at the one or more--

Signed and Sealed this
Fourth Day of February, 2014

Michelle K. Lee
*Deputy Director of the United States Patent and Trademark Office*